United States Patent [19]

Baldwin

[11] Patent Number: 4,996,313
[45] Date of Patent: Feb. 26, 1991

[54] PENICILLINS

[75] Inventor: Jack E. Baldwin, Oxford, England

[73] Assignee: National Research Development Corporation, England

[21] Appl. No.: 438,622

[22] Filed: Nov. 17, 1989

Related U.S. Application Data

[63] Continuation of Ser. No. 933,535, Nov. 21, 1986, abandoned.

[30] Foreign Application Priority Data

Nov. 26, 1985 [GB] United Kingdom ............... 8529063

[51] Int. Cl.$^5$ .................. C07D 499/42; A61K 31/43
[52] U.S. Cl. .................................. 540/312; 514/192; 514/195
[58] Field of Search ............................ 540/312, 310

[56] References Cited

U.S. PATENT DOCUMENTS 3,399,207  8/1968  Bamberg et al. .................... 540/312

FOREIGN PATENT DOCUMENTS 0174129  8/1986  European Pat. Off. .

OTHER PUBLICATIONS

Justus Liebigs Annalen der Chemie, vol. 12, No. 2, pp. 129–1936, Verlag Chemie GmbH, Weinheim (and translation).
Bahatur et al., I. Chem. Soc., 1981, pp. 917–919.
Bhadur et al., J. Amer. Chem. Soc. 103, (1981), pp. 7650, 7651.
Shields et al., Helv. Chim. Acta. 67, (1984), pp. 870, 871.
A. Burger, Medicinal Chemistry, 3rd Ed., Pt. I, Wiley, p. 75.
Remington's Pharmaceutical Sciences, 15th Ed., Mach, p. 466.
Dürckheimer et al., Angew. Chem. 97, (1985), p. 183.
Schröder et al.: Arzneimittelchemie, pp. 32, 33.
Mager: Multidimensional Pharmcochemistry, p. 33.
Römpps Chemie-Lexikon, 8th Ed., p. 1968.

*Primary Examiner*—Nicholas S. Rizzo
*Attorney, Agent, or Firm*—Jacobs & Jacobs

[57] ABSTRACT

A compound of formula II:

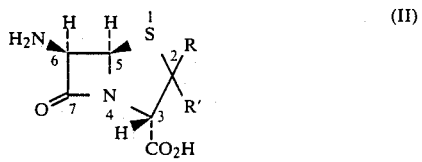

wherein R is hydrogen or an alkyl group and R' is an alkoxy group, and salts and esters thereof.

9 Claims, No Drawings

PENICILLINS

This is a continuation of Ser. No. 933,535 filed Nov. 21, 1986, now abandoned.

This invention relates to antibiotics and in particular to intermediates for the production of novel beta lactam antibiotics.

The beta lactams constitute a group of antibiotics of particular interest into which considerable research has taken place with the aim of producing new antibiotic compounds. In UK Patent Application No. 8421279 a group of novel beta lactam antibiotics is described of the formula

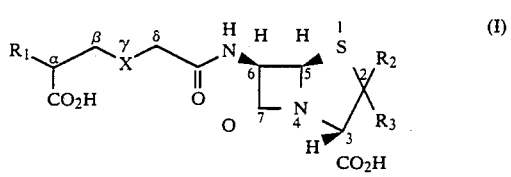

wherein X is sulphur or methylene, $R_1$ is hydrogen, amino or an acylated or carbamylated amino group, $R_2$ is hydrogen or an alkyl group and $R_3$ is an alkoxy group.

Such penicillin compounds (I) are of course very unusual in that they contain an alkoxy group and either hydrogen or an alkyl group at the 2-position of the penam ring system instead of the usual two alkyl (methyl) groups. However, although penicillins containing an alkoxy group at the 2-position are therefore of some interest, the route to a compound of formula (1) described in UK Patent Application No. 8421279 requires a tripeptide which is convertible to the compound through the action of the enzyme isopenicillin N synthetase, thereby placing a considerable restriction upon the nature of the acylamino group which may be present at the 2-position of the penicillin ring. However despite the considerable problems arising from the sensitive nature of the penicillin ring system, we have now found that it is possible to deacylate such penicillins (1) to produce the corresponding compounds (II) containing an amino group at the 6-position of the penam ring system. These compounds (II) are valuable intermediates for the production of alternative antibiotic compounds to those of formula (1) in which different acylamino groups are present at the 6-position.

Accordingly the present invention comprises a compound of the formula

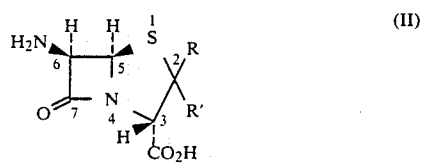

wherein R is hydrogen or an alkyl group and R' is an alkoxy group, and salts and esters thereof.

It will be appreciated that in compounds (II) which are not in salt or ester form, the amino and carboxy group will usually exist in the zwitterion form ($H_3N^+$— and —$CO_2^-$).

Among the penicillins (II), R is preferably an alkyl group. The alkyl groups R and the alkyl groups contained in the alkoxy groups R' may be branched or particularly straight chain, R and R' each conveniently being selected from groups of 1 to 5 carbon atoms, particularly of 1 to 4 and especially of 1 to 3 carbon atoms. Examples of preferred groups R and R' are isopropyl, propyl, particularly ethyl and especially methyl, and isopropoxy, propoxy, particularly ethoxy and especially methoxy.

It may be advantageous, for example in order to increase water solubility, for the penicillins (II) to be in the form of a salt thereof. Such salt formation may involve the amino group and an inorganic or organic acid or the carboxyl group and an inorganic or organic base, the hydrochloride salt and the sodium, potassium and ammonium salts of the penicillin compounds (II), for example, being of some interest Alternatively, it may be advantageous, in order to increase organic solvent solubility or for other reasons, for the penicillin (II) to be in the form of an ester derivative of the 3-carboxy group. Such ester derivatives will contain a group $CO_2R^1$ at the 3-position where $R_1$ is an organic group which may be of a wide variety of types, including those present in known penicillins. Thus, for example, $R_1$ may be an aryl group, or particularly an aryloxyalkyl or alkoxyalkyl group, or especially an aralkyl or alkyl group. The aryl groups contained in such ester groups may be substituted or unsubstituted, substituted and especially unsubstituted phenyl groups being of particular interest. The alkyl and alkoxy groups may be of various sizes but those being or containing straight or branched chains aliphatic hydrocarbon groups of 1 to 10, especially 1 to 5 carbon atoms, are of particular interest. Specific examples of groups $R_1$ which may be present in the ester group of a penicillin (II) are methyl, ethyl, propyl, isopropyl, benzyl, diphenylmethyl, benzyloxymethyl, 2,2,2-trichloroethyl and trimethylsilyl.

As regards the stereochemistry of the penicillins (II), there are two possible configurations at the asymmetric carbon atom to which the groups R and R' are attached, depending on whether the group R or the group R' is in a similar spatial disposition to the adjacent carboxyl group. The latter alternative is of greater interest, especially in the case where R is alkyl, particularly in view of the greater ease of preparation of this stereoisomer.

Specific penicillins according to the present invention are the compounds (II) in which R is hydrogen, methyl or ethyl, and R' is methoxy or ethoxy, including particularly compounds in which R is hydrogen or especially methyl and R' is methoxy such as 2-methoxy-2-methyl-6-amino-3-carboxypenam and 2-methoxy-6-amino-3-carboxypenam. These specific penicillins (II) are of particular interest, especially where they contain a group R which is alkyl, as the stereoisomer in which the alkoxy and carboxy groups at the 2- and 3-positions of the thiazolidone ring have a similar spatial disposition, being in the cis configuration, i.e. as the 2S-isomer. The structure of the compound 2S-2-methoxy-2-methyl-6-amino-3-carboxypenyl is illustrated below in formula (III).

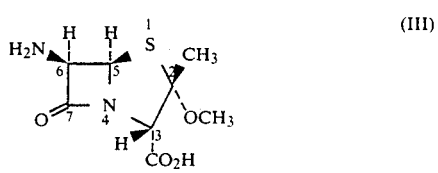

The penicillins (II) may conveniently be prepared by the deacylation of a penicillin (I) containing groups $R_2$ and R₃ at the 2-position which correspond to the groups R and R' at the 2-position of the penicillin (II). The most suitable penicillins (I) for this purpose are those containing a group at the 6-position in which $R_1$ is amino, and conveniently in which X is methylene, the group preferably being of the L-configuration, i.e. those penicillins containing a 6-δ-(L-α-aminoadipamido) group [$R_1 = NH_2$ and $X = CH_2$ in (I)] are of particular value.

The deacylation of a δ-(α-aminoadipamido) or like group substituted on the penicillin ring system presents considerable problems. Direct acidic and alkaline methods of amide hydrolysis are not applicable as these would destroy the sensitive ring system. The use of the "iminochloride" method is not suited to this particular situation since it requires preliminary protection of both of the carboxyl groups and of the primary amino group before it can be applied. Moreover, the conventional bacterial deacylase enzymes frequently used for such sensitive deacylation reactions are not, in general, applicable in the case of hydrophilic groups such as the δ-(α-aminoadipamido) group. Although enzymatic methods of deacylation are potentially attractive in the present context they will therefore require the use of non-conventional enzymes, such as a particular deacylase enzyme which is present in Penicillium chrysogenum, and it is a particular chemical method which has so far proved most effective. This involves the use of a nitrosyl halide reagent, for example nitrosyl bromide or particularly nitrosyl chloride, to form an iminolactone in which the carbonyl oxygen atom of the 6-acylamino group is linked to the u carbon atom of the compound (I) from which the amino group has been lost during formation of the iminolactone, which iminolactone is then cleaved to form the penicillin (II) and a lactone by-product. The reaction of the penicillin (I) with the nitrosyl halide may conveniently be carried out in a suitable solvent system such as acetonitrile under an inert atmosphere such as nitrogen at a temperature in the range of $-10°$ to $+10°$ C., for example at 0° C., the nitrosyl halide conveniently being added in an organic acid such as glacial acetic acid and a reaction period of 5 to 10 minutes generally being suitable Following this, the intermediate iminolactone is cleaved, a suitable reagent for this purpose being a primary alcohol, for example a $C_{1-5}$ alkanol such as methanol, which may conveniently be added to the product obtained by the removal of the solvent from the nitrosyl halide reaction mixture to give a solution which is allowed to stand at room temperature, for example at 20° to 30° C. for a period of 5 to 10 minutes. A convenient working up procedure for isolation of the penicillin (II) involves evaporation, treatment of the residue with a pH 2 buffer, neutralisation with ammonium hydrogen carbonate, freeze drying and high pressure liquid chromatography.

As regards the stereochemistry of the penicillin (I) used to prepare the penicillin (II), it has been found that the stereochemical arrangement of the groups R₂ and R₃ of the penicillin (I) is generally retained during the deacylation to give a penicillin (II) with a similar arrangement of the groups R and R'. The penicillins (I) in which $R_1$ is hydrogen or amino, as described in UK Patent Application No. 8421279 are themselves prepared by the action of isopenicillin N-synthetase on the corresponding tripeptide of formula

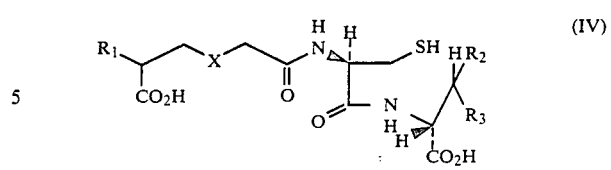

wherein X is sulphur or methylene, $R_1$ is hydrogen or amino, $R_2$ is hydrogen or an alkyl group and $R_3$ is an alkoxy group. When $R_2$ is an alkyl group the carbon atom to which the groups $R_2$ and $R_3$ are attached will be asymmetric and it has been found that efficient conversion of the tripeptide (IV) to the penicillin (I) with isopenicillin N synthetase occurs only with the tripeptide having the R-configuration at the 2-position, this configuration being retained during the conversion to give the stereochemically equivalent penicillin having the S configuration at the 2-position. When $R_2$ is hydrogen, this carbon atom is not asymmetric and it is believed that the penicillin (I) obtained in this case is a mixture of the two stereoisomeric forms differing in the configuration at the 2-position. For this reason the penicillins (I) of most interest, in which $R_2$ is an alkyl group rather than hydrogen, are more readily prepared in the form which has the S-configuration at the 2-position.

The present invention thus includes a process for the preparation of a compound of formula (II) as described hereinbefore which comprises deacylating the corresponding compound of formula (I) in which $R_1$ is hydrogen or preferably amino and X is sulphur or preferably methylene, for example by the use of a nitrosyl halide to form an intermediate iminolactone in which $R_1$ is hydrogen, which iminolactone is subsequently cleaved.

Compounds (II) in salt form may conveniently be prepared by reaction of the free compound with the appropriate acid or base whilst those in ester form may conveniently be prepared by reaction of an alkali metal salt in dimethylformamide with the appropriate halide, or by other conventional methods which avoid reaction with the amino group at the 2-position.

As mentioned previously, the penicillins (II) are of use as intermediates in the production of new penicillins through acylation of the amino group at the 6-position. Various acyl groups R may be introduced, R being an organic acid radical and in particular an organic carboxylic acid radical The halides, especially chlorides and bromides, or anhydrides of the acid group to be introduced are particularly suitable as acylating agents, although other acylating agents may also be used. Such other acylating agents include mixed anhydrides, activated esters and carboxylic acids with carbodiimides. A procedure which is of particular value in many cases involves the use of an organic acid halide, for example an organic carboxylic acid halide such as phenylacetylchloride, an excess of which may conveniently be reacted with the penicillin (II) in a suitable solvent system such as acetone at a temperature in the range of $-5°$ to $+5°$ C., for example at 0° C., a reaction period of 10 to 20 minutes often being suitable.

The present invention thus includes a method of preparing 6-acylamino-2-alkoxy- and 6-acylamino-2-alkoxy-2-alkyl-3-carboxypenams which comprises subjecting a penicillin of formula (II) to the action of an organic acid acylating agent to convert the amino group at the 6-position therein to a group RNH- in which R is an organic acid radical.

The invention is illustrated by the following Examples.

EXAMPLE 1

Preparation of 2S-2-methoxy-2-methyl-6-amino-3-carboxypenam 2S-2-Methoxy-2-methyl-6-δ-(L-α-aminoadipamido)-3-carboxypenam[1] (1.15 mg) in dry acetonitrile (300 μl) is treated at 0° C. under nitrogen with nitrosyl chloride in glacial acetic acid (25 μl, 0.61M). After standing for 5 minutes at 0° C. the solution is evaporated to dryness at 0° C. The residue is treated with methanol (400 μl) and the resultant solution is allowed to stand for 5 minutes at 20° C. and is then evaporated to dryness. Aqueous 0.04M HCl/0.16M KCl pH 2 buffer (400 μl) is added to the residue and the resultant solution is allowed to stand for 3 minutes at 20° C. before aqueous ammonium hydrogen carbonate (300 μl, 70 mM) is added and the solution freeze dried. The freeze dried material is purified by direct h.p.l.c. on a reverse phase octadecylsilane column, using 50 mM aqueous ammonium hydrogen carbonate:methanol (19:1 v/v) as eluant, to give 2S-2-methoxy-2-methyl-6-amino-3-carboxypenam as a freeze dried solid (50 μg, 7%-unoptimised), $^1$H n.m.r. (500 MHz, deuterated Na$^2$H$_2$PO$_4$/Na$_2$HPO$_4$/KCl pH 7.0 buffer, referred to (CH$_3$)$_3$SiCD$_2$CD$_2$CO$_2$Na=0.00, δ values, p.p.m.) 1.91 (3H, s, 2-β-CH$_3$), 3.40 (3H, s, OCH$_3$), 4.36 (1H, s, 3H) 5.36 (1H, d, J 4H$_z$, β-lactam-H, the other β-lactam-H being obscured by HO$^2$H).

[1] 2-Methoxy-6-amino-3-carboxypenam may be prepared in a similar manner starting from 2-methoxy-6-δ-(L-α-aminoadipamido)-3-carboxypenam.

PREPARATION OF STARTING MATERIALS (A)

2S-2-Methoxy-2-methyl-6-δ-(L-α-aminoadipamido)-3-carboxypenam

Preparation of δ-(L-α-aminoadipyl)-L-cysteinyl-(2R,3R-2-amino 3-methoxybutanoic acid)

(1) 2R,3R- and 2S,3S-2-Bromo-3-methoxybutanoic acid

Crotonic acid (8.6 g, 100 mmol) is dissolved in methanol (50 ml) and N-bromacetamide (13.8 g, 10 mmol) is added in portions over 30 minutes. The solution is stirred at 25° C. for 15 hours and the solvent is then evaporated and the residue partitioned between diethyl ether and water. The ether layer is dried (Na$_2$SO$_4$), filtered, evaporated and the residue distilled to yield the title compounds as a colourless oil (14.3 g, 72%), b.p. 88°-89°/0.5 mm.

(2) 2R,3R- and 2S,3S 2-Amino-3-methoxybutanoic acid 2R,3R- and 2S,3S 2-Bromo-3-methoxybutanoic acid (14 g, 71 mmol) are dissolved in ammonia (s.g. 0.88, 250 ml) and the mixture heated in an autoclave at 95° C. for 8 hours. The mixture is cooled to 25° C., evaporated, and the residue suspended in acetone. The resultant colourless solid is filtered off and washed with acetone to give the title compounds as a colourless solid containing residual ammonium bromide, (12.1 g) m.p. 180°-184° C. (dec.).

(3) 2R,3R- and 2S,3S- N-Benzyloxycarbonyl-2-amino-3-methoxybutanoic acid, benzyl ester 2R,3R- and 2S,3S 2-Amino-3-methoxybutanoic acid (3.1 g) are dissolved in a mixture of 1M sodium hydroxide (27 ml), water (20 ml), and dioxan (40 ml). Benzyl chloroformate (3.8 ml, 22 mmol) in dioxan (20 ml) and 1M sodium hydroxide (27 ml) are added to the solution individually, each at the same rate of addition, over 25 minutes. The mixture is stirred for 1 hour, extracted into ethyl acetate (3×200 ml), acidified to pH 1 with 2N hydrochloric acid and then re-extracted into ethyl acetate (3×200 ml). The combined organic extracts are dried, filtered, and evaporated to give an oil. This oil is dissolved in dry dimethyl formamide (20 ml) and to the solution are added sodium hydrogen carbonate (3.14 g, 41 mmol), benzyl bromide (3.8 ml, 33 mmol), anhydrous sodium sulphate (200 mg) and sodium iodide (10 mg), the whole being stirred at 25° C. for 24 hours. The mixture is then extracted into dichloromethane (200 ml), washed with water (4×300 ml), dried (sodium sulphate), filtered and evaporated. Purification by chromatography on silica gel using ethyl acetate and petroleum ether as consecutive eluants gives the title compounds as a colourless oil (4.2 g, 65%) which solidifies on standing, m.p. 44° C.

(4) 2R,3R- and 2S,3S-2-Amino-3-methoxybutanoic acid, benzyl ester 2R,3R- and 2S,3S-N-Benzyloxycarbonyl-2-amino-3-methoxybutanoic acid, benzyl ester (500 mg, 1.4 mmol) are dissolved in dry dichloromethane (3 ml) and hydrobromic acid (45% in acetic acid, 2 ml) is added. The mixture is stirred under argon for 20 minutes and is then evaporated. The residue is dissolved in dichloromethan (3×3 ml) and re-evaporated (3x) to give a further residue which is dissolved in xylene (2×3 ml) and re-evaporated (2x). Petroleum ether (5 ml) is then added and the product is triturated for 5 minutes before discarding the mother liquor and dissolving the solid residue in dichloromethane (5 ml). Triethylamine (1 ml) is added to the dichloromethane solution which is then stirred for 2 minutes and evaporated. The residue is dissolved in dichloromethane (3×5 ml) and re-evaporated (3x) to give a further residue which is triturated with diethyl ether (5 ml). The resulting solid is filtered off, re-extracted with diethyl ether (2×5 ml) and the ethereal layers combined and evaporated to yield the title compounds as a colourless oil (290 mg, 93%).

(5) (N-Benzoyloxycarbonyl-α-benzyl-δ-L-aminoadipyl)-S-benzyl-L-cysteinyl-(2R-,3R-2-amino-3-methoxybutanoic acid), benzyl ester 2R,3R- and 2S,3S 2-Amino-3-methoxybutanoic acid, benzyl ester (177 mg, 0.79 mmol) are dissolved in dry dichloromethane (10 ml) and 2-ethoxy-N-ethoxycarbonyl-1,2-dihydroquinoline (195 mg, 0.79 mmol) and N-benzyloxycarbonyl-α-benzyl-δ-(L-α-aminoadipyl)-S-benzyl-L-cysteine (456 mg, 0.79 mmol), prepared as described by Baldwin et al, Journal of the Chemical Society, Perkin I, 1981, 2253), and sodium sulphate (100 mg) are added and the mixture stirred for 24 hours. The solution is evaporated, the residue is dissolved in ethyl acetate (150 ml), and the ethyl acetate solution washed in turn with 2M hydrochloric acid (50 ml), saturated sodium hydrogen carbonate solution (50 ml) and brine (50 ml), then dried, filtered and evaporated. Purification by chromatography on silica using ethyl acetate and hexane as consecutive eluants gives the title compound as a colourless solid (180 mg, 29%), m.p. 116°-118°; $[\alpha]_D^{20}$—11.7° (c 1, CHCl$_3$) (the 2R,3R compound is less polar than the other, 2S,3S, isomer).

(6) δ-(L-α-Aminoadipyl)-L-cysteinyl-(2R,3R-2-amino-3-methoxybutanoic acid)

N-Benzyloxycarbonyl-α-benzyl-δ-(L-α-aminoadipyl)-S-benzyl-L cysteinyl-(2R,3R-2-amino-3-methoxybutanoic acid), benzyl ester (200 mg, 0.26 ml) is dissolved in tetrahydrofuran (10 ml) and dry liquid ammonia (30 ml). Sodium is added in small portions until a permanent blue colouration remains for 10 minutes and the solution is then quenched by the addition of dry ammonium sulphate until colourless. The solvent is evaporated, the residue is dissolved in 50 mM sulphuric acid (20 ml) and Hopkins reagent (0.05 ml, Baldin et al, ibid) is added The pH is raised to 4 using ammonium hydroxide and the resultant precipitate is washed with water (3×20 ml), then suspended in water (10 ml) and treated with an excess of hydrogen sulphide. Filtration to remove mercuric sulphide and freeze drying gives the title compound [2] as a white solid (67 mg, 68%), $^1$H n.m.r (D$_2$O, referred to external tetramethylsilane - TMS, δ values, p.p.m) 1.05 (3H, d, J 8 Hz), 1.60–1.90 (4H, m), 2.25 (2H, t, J, 8 Hz), 2.80 (2H, m), 3.25 (3H, s), 3.75–3.90 (2H, m) and 4.40 (1H, m).

[2] The yield of the compound is estimated by the addition of a known quantity of dioxan, followed by n.m.r. integration of the standard against the 1.05 signal (the CHCH$_3$ protons). By this method a residual quantity of about 10% of ammonium salt is usually detected in the tripeptide. This contaminant will similarly yield the methoxylated penicillin upon incubation with isopenicillin N synthetase enzyme as described in Example 3.

Preparation of purified isopenicillin N synthetase

Cells of Cephalosporin acremonium C0728 are grown as described by Fawcett et al, (Biochem. J., 1976, 157, 651–660) with the variation that distilled water is used instead of tap water. The isopenicillin N synthetase is isolated in purified form by the following steps, which are carried out at 2°–4° C.

(1) Crude extract

Mycelia (96 hours old/about 10 hours from the beginning of stationary phase) are harvested by filtration through a double-layer of cheese cloth. The cells collected are resuspended in 3×(v/w) distilled water and suction-dried through Whatman filter paper (No. 52) in a Buchner funnel. The suction-dried mycelia are suspended in approximately 3×(v/w) of 50 mM Tris-HCl buffer, pH 8.0, and disrupted in a Dyno Mill (Willy A Bacofen AG Maschinenfabrik, Basel) with 500 ml of 0.25 mm glass beads, being stirred at 3000 r.p.m. in the 600 ml glass head.

(2) Protamine sulphate fractionation

To the above homogenate, a one fifth volume of protamine sulfate solution (6% w/v in distilled water) is added. The resulting solution is stirred for 20 minutes and centrifuged at 10,000 g for 30 minutes to remove precipitate.

(3) Ammonium sulphate fractionation

The supernatant collected above is brought to 55% saturation with ammonium sulphate (Sigma Grade 1) and the precipitate is removed by centrifugation at 10,000 g for 30 minutes. The supernatant is then brought to 85% saturation with ammonium sulphate and enzyme protein is recovered as a precipitate after centrifugation at 10,000 g for 45 minutes.

(4) Sephadex G75 column chromatography

The precipitate obtained after 55–85% ammonium sulphate fractionation is dissolved in a minimum amount of Tris-HCl buffer (50 mM, pH 7.5, 0.015% w/v sodium azide) the final protein concentration being about 40 mg/ml. 80 ml of this protein solution is loaded onto a Sephadex G-75 (Pharmacia, coarse) column (3.7 cm×110 cm) which has been pre-equilibrated with the same Tris-HCl buffer. The fractions with isopenicillin N synthetase activity are pooled and enzyme protein is concentrated by precipitation with 85% w/v ammonium sulphate followed by centrifugation at 10,000 g for 45 minutes.

(5) DEAE Sepharose CL-6B column chromatography

A highly purified enzyme preparation is obtained through ion-exchange chromatography of the enzyme fractions from Sephadex G75 column chromatography. The active fractions are pooled and loaded directly onto a DEAE-Sepharose CL-6B column (5 cm×11.5 cm) which has been pre-equilibrated with Tris-HCl buffer (50 mM, pH 7.5, 0.015% w/v sodium azide). The column is washed with about 500 ml of 50 mM NaCl in the same Tris-HCl buffer to remove unbound material The column is then subjected to a gradient elution of NaCl in buffer (50 mM→250 mM, total volume 800 ml, linear gradient), enzyme activity being eluted at about 100 mM NaCl. The preparation of the enzyme as obtained from the column is suitable for direct use.

The activity of an amount of the enzyme may be quantitatively expressed in units of isopenicillin N synthetase activity, one such unit being defined as that amount of enzyme activity required to form 1 μ mole of isopenicillin N per minute at 27° C. in a standard assay procedure employing incubation conditions similar to those described above.

Preparation of 2S 2-methoxy-2-methyl-6-δ-(L-α-aminoadipamido)-3-carboxypenam

δ-(L-α-Aminoadipyl)-L-cysteinyl-(2R,3R -2-amino-3-methoxybutanoic acid (210 μg: prepared as described above is incubated with purified isopenicillin N synthetase (1.1 units, obtained as described below) in the presence of the cofactors dithiothreitol (2.11 mM), ascorbic acid (1.06 mM), ferrous sulphate (0.11 mM) and catalase (bovine liver, 1800 sigma units) in tris-HCl buffer (50 mM, p 7.5; tris stands for 2-amino-2-hydroxys:ethylpropane 1,3-diol) to a total volume of 1 ml, the incubation being carried out at 27° C. in a shaker (250 r.p.m.) with exposure exposed to the air for 30 minutes. The protein is precipitated from the mixture by the addition of acetone to a concentration of 70% by volume of acetone, then separated by centrifugation and the supernatant freeze dried. The freeze dried material is redissolved in water (500 μl) and the product purified by HPLC (Waters:Z Module Radial Compression Separator System with Radial-Pak C$_{18}$10 cartridge) using 90% 50 mM KH$_2$PO$_4$/10% methanol by volume as the eluting solvent and detecting the antibiotic by its absorption at 220 mm. The product which is thus obtained is freeze dried immediately to provide the title compound.

The freeze dried material has the following the n.m.r. spectrum, the assignment of the various signals to protons in the structure (IV) shown hereinbefore being as follows:

| Signal | Protons |
| --- | --- |
| 1.47 | γ—CH$_2$— |
| 1.64 | β—CH$_2$— |
| 1.74 | CH$_3$— at C-2 |
| 2.15 | δ—CH$_2$ |
| 3.13 | CH$_3$O— at C-2 |
| 3.49 | α—CH— |
| 4.24 | H-3 |

| Signal | Protons |
| --- | --- |
| 5.16 | H-5 |
| 5.32 | H-6 |

Nuclear Overhauser experiments confirm the stereochemistry of the compound at the 2-position as indicated in the title of the Example Thus, irradiation of the singlet at 1.74 p.p.m. (methyl group) gives an enhancement (typically 19%) in the difference spectrum of the signal at 4.24 p.p.m. (H-3) which is consistent with a methyl group in the $\beta$-configuration (for Isopen N and Pen G the corresponding enhancement observed on irradiation of a $\beta$-methyl group is typically 21 and 25%, respectively). The mass spectrum of the compound obtained under Fast Atom Bombardment (FAB) conditions shows a molecular ion [MH+] 376 m/e. The base peak in the spectrum at 321 m/e is a characteristic penicillin fragment:

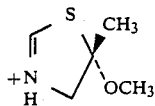

(B) 2-Methoxy-6-δ-(L-α-aminoadipamido)-3-carboxypenam

Preparation of
δ-(L-α-aminoadipyl)-L-cysteinyl-(D-serine-O-methyl ether (1) N-p-Methoxybenzyloxycarbonyl-D-serine benzyl ester N-p-Methoxybenzyloxycarbonyl-D-serine (5.39 mg, 2.00 sm:ol; prepared as a colourless solid of m.p. 96°–97° C. in 60% yield by the dissolved in methanol and treated with a solution of potassium carbonate (138 mg, 1.00 mmol) in water (2 ml). The mixture is evaporated by dryness, N,N-dimethyl-forimide (DMF) is added and re-evaporated (2×2 ml), and the solid residue is then dissolved in dry warm DMF, benzyl bromide (248 μl, 2.1 mmol) is added and the solution is warmed in a dry closed flask at 50° C. for 1 hour. The resulting mixture is portioned between ether (10 ml) and water (10 ml) and the aqueous layer is extracted with ether (2×10 ml). The combined ether extracts are washed with saturated sodium bicarbonate (5 ml) and saturated brine (5 ml), dried and evaporated to dryness. The residue is purified on a column of silica gel using 1:1 v/v ethyl acetate:petroleum ether as eluant to·yield to title compound as a homogenous oil (590 mg, 82%) which crystallises on standing to give a colourless solid of m.p. 67°–68° C. (from diethyl ether); $[\alpha]_D^{20}$—6.3° (c 4.0, CHCl$_3$).

(2) N-p-Methoxybenzyloxycarbonyl-O-methyl-D-serine benzyl ester

The N-p-methoxybenzyloxycarbonyl-D-serine benzyl ester (720 mg, 2.00 mmol) is dissolved in dry dichloromethane (20 ml) and the solution cooled in dry ice/acetone. Boron trifluoride etherate (100 μl) is added followed by the portionwise addition of diazomethane (30 mmol in 20 ml CH$_2$Cl$_2$) After about 30 minutes the solution is filtered and washed once with water (10 ml), then dried (MgSO$_4$) and evaporated to dryness. The resulting residue is chromatographed on silica gel using chloroform as eluant to give the pure title compound as an oil (520 mg, 70%) which crystallises on standing to give a colourless solid of m.p. 68°–69° C.; $[\alpha]_D^{20}$—1.3° (c 4.0, CHCl$_3$).

(3) O-Methyl-D serine benzyl ester, hydrochloride

To N-p-methoxybenzyloxycarbonyl-0-methyl-D-serine benzyl ester (130 mg, 0.35 mmol) is added a mixture of cold trifluoroacetic acid (TFA): anisole (4.8:1 v/v) (0.6 ml). The mixture is shaken on an ice bath until all the solid has dissolved and the TFA is then evaporated initially on a rotary evaporator at 0° C., finally using a high vacuum pump. The resulting residue is purified by chromatography on silica gel using 98:2 v/v chloroform:methanol as eluant to give the title compound in basic form as a yellowish oil (38 mg, 55%); this is converted to the hydrochloride salt which is a white solid, m.p. 100°–101° C., $[\alpha]_D^{20}$+15.5° (c 2.0, CH$_3$OH).

(4) (N-Benzyloxycarbonyl-α-benzyl-δ-L-α-aminoadipyl)-(S-benzyl-L-cysteinyl)-(O-methyl-D-serine benzyl ester)

(N-Benzyloxycarbonyl-benzyl-6-L-α-aminoadipyl)-S-benzyl-L-cysteine (150 mg, 0.26 mmol, prepared as described by Baldwin et al, ibid) and O-methyl-D-serine benzyl ester, hydrochloride salt, (63 mg, 0.26 mmol) are dissolved in dichloromethane (8 ml) containing triethylamine (36 ul, 0.26 mmol). 2-Ethoxy-N-ethoxycarbonyl-1,2-dihydroquinoline (64 mg) is added and the solution is stirred for 24 hours. The solution is then evaporated, the residue dissolved in chloroform (10 ml), the chloroform solution washed in turn with 0.1M hydrochloric acid (10 ml) and saturated sodium hydrogen carbonate solution (10 ml), dried (MgSO$_4$), filtered and evaporated. Purification by chromatography on silica gel using 98:2 v/v chloroform:methanol as eluant gives the title compound (150 mg, 76%) which is crystallised from ethyl acetate to give a colourless solid of m.p. 151°–152° C., $[\alpha]_D^{20}$—13.9° (c 1.0, CHCl$_3$); $^1$H n.m.r (CD$_3$CN, referred to external TMS, δ value, p.p.m.) 1.5–2.3 (includes solvent peaks), 2.72 (2H, ABX octet, $J_{AB}$13.5, $J_{AX}$7.4 and $J_{BX}$5.0 Hz) 3.25 (3H, s), 3.56 (1H, A part of ABX, $J_{AB}$9.2, $J_{AX}$3.2 Hz), 3.73 (3H, s), 3.77 (1H, B part of ABX, $J_{BX}$4.0 Hz), 4.2, 4.52, 4.60 (3×1H, m), 5.1 (6H, m), 6.13, 6.68, 7.17 (3×1H), 7.35 (20H, m).

(5) δ-(L-α-Aminoadipyl)-L-cysteinyl-(D-serine-O-methyl ether)

(N-Benzyloxycarbonyl-α-benzyl-δ-L-α-aminoadipyl)-(S-benzyl-L-cysteinyl)-(O-methyl-D-serine benzyl ester) (80 mg, 0.10 mmol) is dissolved in tetrahydrofuran (1 ml) and dry liquid ammonia (30 ml). Sodium is added in small portions until the solution is permanently blue for 5 minutes, the solution then being quenched with dry ammonium sulphate until colourless. The solvent is evaporated and the residue is dissolved in water (5 ml). Ammonium hydroxide is added to the solution to raise the pH to 8 and oxygen gas is then bubbled through it for 4 hours. Purification by preparative electrophoresis (pH 3.5, 3 Kv, 2 hours) gives the title compound in its disulphide form (10 mg, 26%) as a colourless solid, $^1$H n.m.r. (D$_2$O, referred to external TMS, δ values, p.p.m.) 1.5–1.8 (4H, m), 2.25 (2H, t, J 7.0 Hz) 2.73 (2H, m), 3.19 (3H, s), 3.65 (2H, ABX, $J_{AB}$10,5 $J_{AX}$3.9, $J_{BX}$5.5 Hz), 3.84 (1H, t, J 6.2 Hz), 4.40 (1H, t, J 5.8 Hz), 4.47 (1H, m).

Preparation of
2-methoxy-δ-6-(L-α-aminoadipamido)-3-carboxypenam

δ-(L-α-Aminoadipyl)-L-cysteinyl-(D-serine-O-methyl ether), prepared as described above is incubated with purified isopenicillin N synthetase obtained as described above, the incubation medium being constituted as follows with the various component solutions being prepared in water.

| | |
|---|---|
| Tripeptide (10 mg/ml) | 100 μl |
| Isopenicillin N synthetase | 6.6 units |
| Ferrous sulphate (5 mM) | 100 μl |
| L-Ascorbic acid (5 mM) | 100 μl |
| Dithiothreitol (100 mM) | 50 μl |
| Catalase (standard preparation, 1/10 diluted) | 43 μl |
| Sodium hydroxide (100 mM) | 30 μl |

The final volume is adjusted to 5 ml with pH 7.5 tris buffer. A control is run in which 100 μl of water replaces the peptide solution. The incubation is carried out at 30° C. in a shaker (250 r.0.m) with exposure to the air for 30 minutes. The protein is precipitated from the mixture by the addition of acetone to a concentration of 70% by volume of acetone, then separated by centrifugation (5,000 r.p.m. for 10 minutes) and the supernatant freeze dried after removal of the acetone in vacuo to give the title compound which is believed to be a mixture of the 2R and 2S isomers.

The freeze dried material has a $^1$H n.m.r. spectrum (250 MHz in $D_2O$ with HOD suppression, referenced to external TMS, δ values p.p.m.) showing the AB-quartet at 5.23, 5.45 (2H, J=3.95 Hz).

EXAMPLE 2

Preparation of 2S-methoxy-2-methyl-6-phenylacetamido-3-carboxypenam 2S 2-Methoxy-2-methyl-6-amino-3-carboxypenam (50 μg) is dissolved in aqueous ammonium hydrogen carbonate (100 mM, 300 μl) and the solution cooled to 0° C. Phenylacetyl chloride (1.5 mg) in acetone (1 ml) is added and the solution is stirred at 0° C. for 15 minutes and then extracted with diethyl ether (2 ml) and the remaining aqueous layer freeze dried. Purification by direct h.p.l.c. on a reverse phase octadecylsilane column, using 50 mM aqueous ammonium hydrogen carbonate:methanol (3:2 v/v) as eluant, gives 2S-2-methoxy-2-methyl-6-phenylacetamido-3-carboxypenam as a freeze dried solid (15 μg, 19% - unoptimised), $^1$H.n.m.r. (500 MHz, $^2H_2O$ pH 7, referred to $(CH_3)_3SiCD_2CD_2CO_2Na=0.00$, δ values, p.p.m.) 1.91 (3H, 2, 2-β-$CH_3$), 3.37 (3H, s, $OCH_3$), 5.39 (1H, d, J4Hz, β-lactam-H), 5.55 (1H, d, J4Hz, β-lactam-H) 7.3–7.4 (5H, m aryl-H).

Bioassay

2S-Methoxy-2-methyl-6-phenylacetamido-3-carboxypenam was dissolved in pH 7.5 Tris buffer and the solution was used for a hole plate inhibit-on assay with *Staphyloccocus aureus* N.C.T.C. 6571. The compound showed antibacterial activity which was destroyed by the action of β-lactamase I from *Bacillus cereus*. This result contrasts with the behaviour of 2S-2-methoxy-2-methyl-6-amino-3-carboxypenam which: showed no antibacterial activity in this assay at a 1 μg level.

What is claimed:

1. A compound of Formula II:

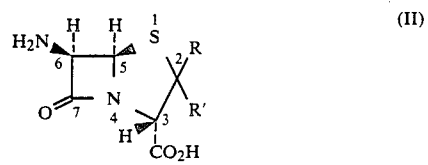

wherein R is hydrogen or an alkyl group of 1 to 5 carbon atoms and R' is an alkoxy group of 1 to 5 carbon atoms, and pharmaceutically acceptable salts and esters thereof.

2. A compound according to claim 1 in which R represents a methyl group.

3. A compound according to claim 1, in which R' represents a methoxy group.

4. A compound according to claim 1 which is 2-methoxy-2-methyl-6-amino-3-carboxypenam or 2-methoxy-6-amino-3-carboxypenam.

5. A compound according to claim 1 in which the alkoxy group at the 2-position has the 2S-conformation and the carboxy group at the 3-position has a similar special disposition.

6. 2S-2-methoxy-2-methyl-6-amino-3-carboxypenam.

7. The compound according to claim 1, wherein said pharmaceutically acceptable ester is a phenyl or alkyl ester.

8. The compound according to claim 1, wherein said pharmaceutically acceptable ester is the phenyl ester.

9. The compound according to claim 1, wherein said pharmaceutically acceptable ester is the methyl, ethyl, propyl, isopropyl, benzyl, diphenylmethyl, benzyloxymethyl, 2,2,2-trichloroethyl or trimethylsilyl ester.

* * * * *